United States Patent
Heier et al.

(10) Patent No.: US 6,797,277 B2
(45) Date of Patent: Sep. 28, 2004

(54) DELIVERY SYSTEM FOR PESTICIDES AND CROP-YIELD ENHANCEMENT PRODUCTS USING MICRO-ENCAPSULATED ACTIVE INGREDIENTS IN EXTRUDED GRANULES

(75) Inventors: John L. Heier, Live Oak, CA (US); David T. Schulteis, Fresno, CA (US)

(73) Assignee: Wilbur-Ellis Company, San Francisco, CA (US)

( * ) Notice: Subject to any disclaimer, the term of this patent is extended or adjusted under 35 U.S.C. 154(b) by 0 days.

(21) Appl. No.: 10/159,213

(22) Filed: May 29, 2002

(65) Prior Publication Data

US 2003/0224031 A1 Dec. 4, 2003

Related U.S. Application Data

(60) Provisional application No. 60/295,393, filed on Jun. 1, 2001.

(51) Int. Cl.$^7$ .............................................. A01N 25/28
(52) U.S. Cl. ........................ 424/408; 424/417; 504/140; 504/271; 514/380
(58) Field of Search ................................. 504/101, 140, 504/271; 71/64.02, 64.05; 424/400, 405, 408, 409, 417–421; 514/380

(56) References Cited

U.S. PATENT DOCUMENTS

| | | | |
|---|---|---|---|
| 3,333,943 A | * | 8/1967 | Richter et al. ................. 71/100 |
| 4,405,357 A | | 9/1983 | Chang |
| 5,443,764 A | * | 8/1995 | Lloyd et al. .................... 264/15 |
| 5,652,196 A | * | 7/1997 | Luthra et al. ................. 504/116 |

FOREIGN PATENT DOCUMENTS

EP 0501798 * 9/1992

OTHER PUBLICATIONS

Information Data Sheet for COMMAND 3ME microencapsulated herbicide, published Jan. 2001.
Information Data Sheet for LONDAX herbicide, published Apr. 1, 1998.
Information Data Sheet for Shark herbicide, published 2000.
Information Data Sheet for WARRIOR insecticide, published 2000.
Information Data Sheet for ORDRAM 8–E selective herbicide, published Mar. 1994.
Information Data Sheet for Abolish 8EC rice herbicide, published 1998.
Information Data Sheet for SEMPRA CA herbicide, published 2000.
Material Safety Data Sheet for IN–PLACE, published Apr. 2001.

* cited by examiner

Primary Examiner—Neil Levy
(74) Attorney, Agent, or Firm—R. Michael West

(57) ABSTRACT

Water-dispersible, extruded granules for delivering agricultural chemicals, such as pesticides or non-pesticidal materials, to a crop. The granules are extrusion-formed from a blended composition including at least one active chemical ingredient, a solid carrier, and a binder. The active chemical ingredient may or may not be micro-encapsulated. The binder may be added directly to the composition or applied as a coating to the granules after the extrusion process. The binder reduces attrition, chemical volatility, and phytotoxicity. The granules are applied to a crop field by aerial means. The dense granules display good vertical drop characteristics, with little drift. If the crop field has standing water, the water-dispersible granules sink and break up, effecting dispersion of the chemical ingredient. When applied to a dry field, the subsequent exposure to water to the granules effects the same dispersal of chemical ingredient.

8 Claims, 1 Drawing Sheet

Figure 1:
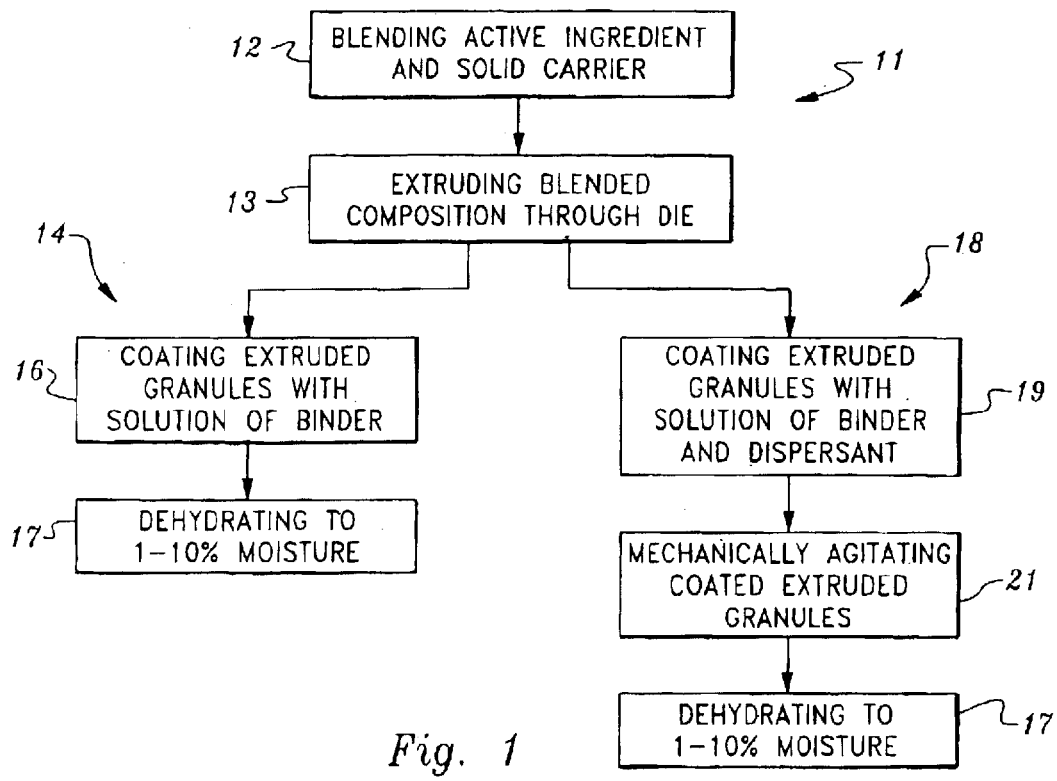

DELIVERY SYSTEM FOR PESTICIDES AND CROP-YIELD ENHANCEMENT PRODUCTS USING MICRO-ENCAPSULATED ACTIVE INGREDIENTS IN EXTRUDED GRANULES

CROSS-REFERENCE TO RELATED APPLICATION

Pursuant to the provisions of 35 U.S.C. Section 119(e), Applicants claim the priority benefits of Provisional Application Serial No. 60/295,393, filed Jun. 1, 2001, entitled Delivery System For Pesticides And Crop-Yield Enhancement Products Using Micro Encapsulated Active Ingredients In Extruded Granules, and assigned to the assignee of the present application.

BACKGROUND OF THE INVENTION

1. Field of the Invention

The invention relates generally to systems for delivering agricultural chemicals, to crop fields. More specifically, the invention pertains to a delivery system for both pesticide products and crop yield enhancement materials, employing water-dispersible extruded granules, manufactured from a uniformly blended composition of at least one active chemical ingredient, a solid carrier, and a binder.

2. Description of the Prior Art

A wide range of agricultural chemicals has been developed to increase agricultural production. Some of these chemicals, generally designated pesticides, are designed to eliminate competing plant growth or parasitic organisms. Consequently, the term pesticide includes a variety of products such as herbicides, insecticides, and fungicides. Another group of products, which is non-pesticidal in nature, is designed to maximize crop yields by acting directly on the crop itself. These non-pesticidal materials include, for example, plant growth regulators, insect growth regulators, micronutrients, and fertilizers.

Agricultural chemical products have been formulated as emulsifiable concentrates, wettable powders, dusts, water dispersible granules, baits, water soluble concentrates, water or oil based suspensions, and impregnated or extruded granules. These chemical products have been delivered to the target site using either ground or aerial equipment, specially adapted to handle the various product forms. For example, spraying equipment is used to deliver both water based dilute and concentrate sprays of active ingredients. Dry application of active ingredients in the form of dusts, baits, and granular products is also employed. And, chemigation, drip-line, and wick application techniques are commonly employed in the industry as well.

The primary, beneficial effects of these agricultural chemicals are sometimes accompanied by secondary effects that detrimentally impact the environment surrounding the crop field. Within that surrounding environment are humans, animals, water, and non-target plants. Secondary effects on the environment increase as the result of: (1) off-target drift of the applied product; and, (2) volatilization of the active chemical ingredient from the applied product.

Off-target drift refers to the tendency of air-borne particles or droplets of product to be carried by wind and air currents off the application site, before settling on the ground or becoming adhered to plant material. Typically, this occurs during the application process itself, but it may also occur after application, if the chemical product is susceptible to being blown off the ground or plant material.

Volatilization of the active ingredient of the product results in the the unwanted airborne transport of vaporized forms of chemicals to adjacent lands, where it may adversely affect humans, animals, and off-target plant materials. Volatilization also necessarily reduces the efficacy of the chemicals applied on the target property, as a portion is lost and applied where it is not intended.

Ground application of chemicals, whether in a spray form or in a dry form, is vulnerable to off-target drift and volatilization. Aerial application, while capable of covering large crop areas relatively quickly, is even more vulnerable to drift and volatilization problems. Owing to the speed and elevation of the plane, and the unpredictability of wind and air currents especially around the margins of the target areas, the chances for unwanted secondary application of chemicals are enhanced by aerial application.

Efforts have been made to reduce drift by increasing droplet size, and to reduce volatalization by encapsulating droplets. The product chemistry of the active ingredients sought to be applied also limit the options on the type of product formulation and the manner of application. For example, the prior art teaches a method of liquid encapsulation of the active ingredient in a plastic or a polymer. U.S. Pat. No. 4,405,357, discloses a liquid encapsulation formulation of an active ingredient, sold under the trademark CLOMAZONE. Liquid encapsulation maintains the active ingredient in relatively large droplet form, reducing airborne drift. In addition, the plastic or polymer outer coating effectively seals off the active ingredient, thereby reducing volatilization and its detrimental effects.

It would be theoretically advantageous to so encapsulate all of the active ingredients in agricultural chemicals, but drawbacks remain. First, the product chemistry of the active ingredients sought to be applied may limit the options on the type of product formulation and the manner of application. Certain active ingredients, individually or in combination with others, are not as suitable for liquid encapsulation as others. Thus, if two or more active ingredients are combined, liquid encapsulation may not reduce the volatilization of the active ingredients as effectively, as with a single active ingredient. An example of this interaction between two active ingredients is the combination of CLOMAZONE and a fertilizer. The fertilizer is a humectant, absorbing water out of the air, thereby increasing the volatility of the CLOMAZONE to the extent that liquid encapsulation is not very effective. Second, liquid encapsulation is quite expensive, so the cost/benefit analysis does not always favor liquid encapsulation as a desired product formulation.

SUMMARY OF THE INVENTION

It has been determined that water-dispersible, extruded granules, containing active chemical ingredients, provide an effective delivery system for both pesticide products and crop-yield enhancement materials. The extruded granules are manufactured from a composition including at least one active chemical ingredient, a solid carrier, and a binder. The active ingredients may be selected from one or more pesticide products, either alone or in combination with a crop-yield enhancing product. The active ingredients may be micro-encapsulated with a plastic or polymer coating, but such micro-encapsulation of the active ingredients is not necessary to practice the invention.

To form the composition, one or more of the active ingredients is first blended uniformly with a solid carrier. The solid carrier is selected from an approved list of "inert ingredients" which can be applied safely with pesticides. The blended composition is then extruded through a die to form small granules of generally uniform size.

The extruded granules are next coated with a liquid solution of an adhesive binder, such as a lignosulfonate material. The binder helps maintain the solid carrier together, and also reduces attrition, or dust-producing abrasive chaffing between the granules. Optionally, a dispersant may be added to the adhesive binder solution. The dispersant assists in the physical disintegration of the granule, and the desirable equal distribution of the inert ingredient, when the granules are immersed in water. Finally, the solution-coated granules are de-hydrated to a moisture content within the range of 1–10%, and preferably about 5%–6%. Then, the extruded granules are ready for use.

The granules are well suited for aerial application to crop fields. They are dry, easy to handle, and do not produce attrition dust. Owing to their relatively high density, the extruded granules fall rapidly, and are not influenced or affected by minor wind currents. Also, the dense granules sink rapidly after they fall into the water, and disintegrate in the water to spread the active ingredient quickly.

BRIEF DESCRIPTION OF THE DRAWINGS

FIG. 1 is a diagrammatic chart, showing two alternative processes for forming coated extruded granules;

FIG. 2 is a diagrammatic chart, showing a first process for forming entirely blended extruded granules; and, FIG. 3 is a diagrammatic chart, showing a second process for forming entirely blended extruded granules with a dispersant.

DETAILED DESCRIPTION OF THE PREFERRED EMBODIMENT

Turning now to FIG. 1, the preferred process 11 for manufacturing the extruded granules of the present invention is shown. In a first step 12, at least one active ingredient is uniformly blended with a solid carrier. The active ingredient may either be a pesticide or a crop-yield enhancement product. Pesticides include a variety of products such as herbicides, insecticides, and fungicides. Representative examples of herbicides include the trademarked products CLOMAZONE, LONDAX, and SHARK.

The crop-enhancement products, which are non-pesticidal in nature, are designed to maximize crop yields by acting directly on the crop itself. These non-pesticidal materials include, for example, plant growth regulators, fertilizers, and micro-nutrients. Examples of plant growth regulators include chloromequat chloride and mepiquat chloride. Examples of micro-nutrients are zinc sulfate and manganese sulfate.

It is contemplated herein that one or more active ingredients may be used, in any desired combination, in making the extruded granules of the present invention. Thus, an herbicide may be paired with an insecticide. Or, an herbicide may be joined with a micro-nutrient. Or, a plant growth regulator may be combined with a fertilizer and a fungicide.

The solid carrier, which is blended with the active ingredient(s), is selected from a list of U.S. Environmental Protection Agency approved "inert ingredients" which can be applied in conjunction pesticides. Applicants prefer to use aluminum silicate, also known as Texas Ball Clay, as their solid carrier. However, practice of the invention is not limited to the use of aluminum silicate for the solid carrier. Other suitable equivalents include: kaolin, montmorillinite, attapulgite, Black Charm Clay, bentonite, corn cob, sand, biodac, starch matrix, fluid earth, carbon, activated carbon, or any other solid diluent which can be extruded while not affecting the chemical nature of the active ingredients. As will be seen from the examples set forth below, the solid carrier provides the bulk of the weight of the extruded granules, and ensures that the density of the granules will be sufficiently high so they will sink quickly in water.

In step 12, the solid carrier is preferably in a micronized, or dry powder form, while the active ingredient(s) is sprayed thereon. Simultaneously, the carrier and the active ingredient are mechanically blended until a uniform consistency is obtained. This uniform distribution of the active ingredient throughout the solid carrier is important in ensuring that the subsequent distribution of the active ingredient when it goes into solution, is also uniform.

In step 13, the thoroughly mixed and blended composition is extruded through a die to form the granules. Using conventional extrusion machinery, containing circular die perforations of approximately 2 mm in diameter, the blended material is first forced through the die and then severed into granule segment lengths of approximately 2 mm. Although the particular configuration and size of the granule are not critical as such, these parameters have been determined as satisfactory in carrying out the invention successfully. Where granule size must be adjusted either upwardly or downwardly in accordance with the teachings which follow below, the size of the die perforations and/or the adjustment of the severing knife are the effective mechanisms to make such adjustments. Those of ordinary skill in the art will recognize that where granule size becomes too small, excessive drift of the granules will result, contrary to the objectives of the invention. And, where granule size becomes too large, disintegration of the granule in water and dispersion of the active ingredient throughout that water, will be slow or ineffective, also inconsistent with objectives of this disclosure.

At this juncture, the process 11 may take one of two different routes. The first route 14, provides that the extruded granules are coated in step 16, with a liquid solution of adhesive binder. One purpose of the binder is to minimize attrition of the granule during transportation and handling of the extruded granule. Attrition refers to abrasive activity between the granules and their container and delivery system, and between the granules themselves. Attrition produces dust and other fine particles which can cause drift and other unwanted distribution of the active ingredient. Another purpose of the binder is to maintain the particles of the solid carrier together, in the granular form which they are extruded. This ensures a more uniform and predictable distribution of the active ingredient in the crop field.

The binder is a lignosulfonate material, and a suitable product is sold under the trademark NORLIG A. Other materials which may be used as a binder include molasses, polysaccarhrides, methylcellulose, acrylic polymers, bentonite, rendering fat, and water soluble glues. Typically, the binder is spray-applied to the granules as they are passed by a spraying station.

In step 17, the coated granules are dehydrated to within a moisture content range of 1–10%. The preferred range is 5%–6%, but the precise optimum moisture content for a particular granule, taking into consideration its size, type of solid carrier, and environment of storage and application, will vary. One of ordinary skill in the art will appreciate that if the moisture content is too high, the binder will be ineffective in maintaining the granules whole, and early disintegration of the granules will result. On the other hand, if the moisture content is too low, the granules will calcify and excessive attrition will result. In addition, too low a moisture content may prevent the granule from disintegrating, dispersing, and releasing the active ingredient.

The process 11 also may be carried out taking a second, alternative route 18. This route contemplates the addition of a dispersant during the granule coating step, and the addition of an agitation step, before dehydration of the granules occurs. To that end, in step 19, the extruded granules are coated with a solution including both a binder and a dispersant. The dispersant is also a lignosufonate material, and the preferred product is marketed under the trademark NORLIG II E. Alternative substitutes for NORLIG II E include condensed napthalene sulfonates, swelling bentonite, and acid/base effervescent systems.

The principal purpose of the dispersant is to accelerate the disintegration of the granule, once it is immersed in water. Depending upon the particular circumstances of application, a dispersant may not be required or desirable. For example, in the use of an insecticide as an active ingredient, a slow rate of ingredient utilization, on the order of seven to fourteen days, may be desirable. In that instance, taking route 14 to carry out the process 11 may be appropriate, so that no dispersant at all is used in the coating solution. But where rapid dispersal of the active ingredient is the objective, so that the active ingredient is deployed in five to ten minutes, the dispersant is selected to effect a rapid breakup of the extruded granules.

In step 21, the coated granules are mechanically agitated for three to five minutes. In this step, the coated granules come into contact with each other and with their support surface so as to enhance thorough and uniform coating. Following step 21, the same dehydrating step 17 is undertaken, to bring the moisture content of the granules within the target range of 1% to 10%. Step 17 is carried out in the same manner and with the same objectives as that previously explained with respect to carrying out route 14.

Figure 2:
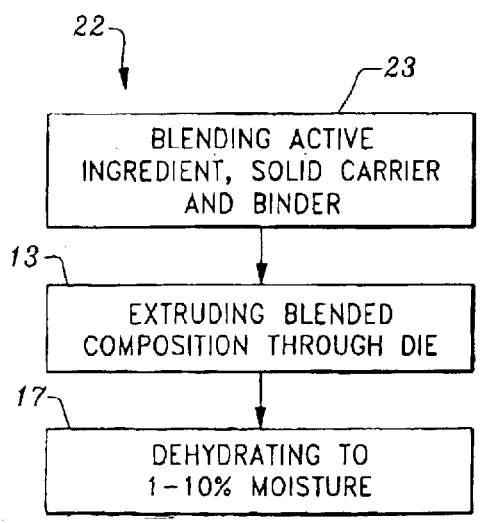
Figure 3:
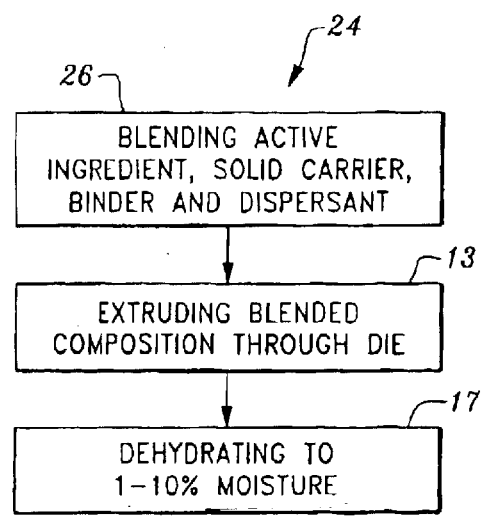

Two other alternative processes, shown in FIGS. 2 and 3, may also be employed to manufacture the extruded granules of the present invention. In carrying out process 22, a first step 23 entails blending at least one active ingredient, a solid carrier, and a binder. The active ingredient, solid carrier, and the binder are identical in nature to those discussed previously. The principal differing feature in this step is the addition of the binder to the blended composition, rather than applying the binder as a coating to the extruded granule. Since the binder is uniformly distributed throughout the composition, the weight proportionate amount of binder may be increased if necessary, to reduce attrition to acceptable levels.

Next, in step 13, the blended composition is extruded through a die, in a manner identical to the set forth above. Lastly, in step 17, the extruded granules are dehydrated to display a moisture content between 1% and 10%.

A process 24, shown in FIG. 3, is very similar to process 22 with a single exception. In an initial step 26, at least one active ingredient, a solid carrier, a binder, and a dispersant are all blended to form a uniform composition. For the same reasons as discussed before, the addition of the water reactive dispersant will accelerate the disintegration of the granule, when it is immersed in water. However, owing to the fact that dispersant is uniformly mixed throughout the solid body of the granule, as opposed to being coated on the exposed portion of the granule, the rate of disintegration will be slower.

The blended composition of active ingredient, solid carrier, binder, and dispersant is extruded through a die, in step 13. As a final step 17, the extruded granules are dehydrated to have a moisture content within the range of 1% to 10%. Having explained the basic processes for producing the extruded granules, we can now turn to some specific examples of granule formulations, as well as discussions regarding field performance studies of the granules.

EXAMPLE 1

A micro-encapsulated liquid formulation of an herbicide, sold under the trademark CLOMAZONE, was sprayed onto a micronized solid carrier of aluminum silicate clay, and blended until a uniform mixture was achieved. The blended composition was then extruded under high pressure through a die provided with 2 mm circular apertures therein. The extruder used was a California Pellet Mill. The knife mechanism of the extruder was set to sever the extruded composition into 2 mm lengths. The extruded 2 mm granules were discharged onto a 30-mesh screen for the removal of fines. The extruded granules were then coated with a solution of a binder and a dispersant. After initial coating was completed, the granules were mechanically agitated for three minutes to equalize and spread the coating evenly over the outer surface of the granules. The granules were then fluid-bed dried until a moisture content of 5%–6% was achieved.

The following ingredients and their respective percentages by weight, were incorporated into the extruded granules of Example 1:

| Ingredient | Function | Percent By Weight |
| --- | --- | --- |
| Clay | Solid Carrier | 80 |
| COMMAND 3 ME [CLOMAZONE] | Active Ingredient | 16 |
| NORLIG A | Binder | 1 |
| NORLIG II D | Dispersant | 1 |
| Water | Mixing Agent | 2 |

The granules produced by following the teachings of Example 1 exhibited a density of 1.15. Owing to the fact that the commercial product of the active ingredient used has an actual concentration of approximately 33%, the resultant percentage of actual CLOMAZONE by weight in the granule was slightly above 5%. With this target concentration, an application rate of twelve pounds of granules per acre results in 0.6 pounds of active ingredient per acre.

Although Example 1 has specific percentages, by weight, for each of the various ingredients, one of ordinary skill in the art will recognize that a practical working range of percentages exists for each of these ingredients. For example, if the amount of active ingredient were increased, say to 26%, and the amount of clay were proportionately decreased, the potency of each granule would increase. To compensate for the more potent granules, the target concentration set forth above of twelve pounds per acre would have to be decreased. However, by reducing the application rate, the number of granules per acre is reduced. To compensate for fewer granules, one of ordinary skill may elect to reduce the size of the granules to increase the number of granules for improved uniformity of dispersal of the active ingredient. Reducing the size of the granules beyond a certain point will increase the chances for off-target drift to an unacceptable level.

An opposite, but similarly derived limit, will result from diluting the active ingredient too much. If the weight percentage of active ingredient were decreased to, say 6%, a greater application rate will be necessary to compensate for the less potent granules. With more granules to disperse than desirable, one of ordinary skill may increase the size of the granules to compensate. Increasing the size of the granules beyond a certain point will slow down disintegration and dispersal of the active ingredient to an unacceptable rate.

As to modifications to the percentages of the binder and dispersant ingredients, the ranges of acceptable percentages are established to some extent by the desired performance characteristics of the extruded granules. Increasing the percentage of the binder to 2% will be more expensive, and it may not reduce attrition sufficiently to be cost justified. On the other hand, reducing the percentage of the binder to 0.1%, may result in granule breakup during storage and transport, and high levels of attrition. Similarly, higher percentages of the dispersant agent may make the active ingredient disperse more quickly, but may not make the active ingredient work more effectively. However, in certain applications, where a very slow dispersal rate is desired, the dispersant agent may be eliminated entirely.

Thus, while Example 1 sets forth particular ingredients and weight percentages, these particulars are set forth solely by way of example, and they are not intended to limit the scope of the claimed invention in any way.

EXAMPLE 2

The composition of Example 1 in which an herbicide is substituted for the CLOMAZONE, as the active ingredient.

EXAMPLE 3

The composition of Example 1 in which an insecticide is substituted for the CLOMAZONE, as the active ingredient.

EXAMPLE 4

The composition of Example 1 in which a fungicide is substituted for the CLOMAZONE, as the active ingredient.

EXAMPLE 5

The composition of Example 1 in which a plant growth regulator is substituted for the CLOMAZONE, as the active ingredient.

EXAMPLE 6

The composition of Example 1 in which a micronutrient is substituted for the CLOMAZONE, as the active ingredient.

EXAMPLE 7

The composition of Example 1 in which a fertilizer is substituted for the CLOMAZONE, as the active ingredient.

EXAMPLE 8

The composition of Example 1 in which an insect growth regulator is substituted for the CLOMAZONE, as the active ingredient.

EXAMPLE 9

The composition of Example 1 in which at least one pesticide is substituted for the CLOMAZONE, as the active ingredient.

EXAMPLE 10

The composition of Example 1 in which at least one crop-yield enhancement product is substituted for the CLOMAZONE, as the active ingredient.

EXAMPLE 11

The composition of Example 1 in which at least one pesticide and at least one crop-yield enhancement product are substituted for the CLOMAZONE, as the active ingredient.

EXAMPLE 12

The composition of Example 1 in which at least two pesticides and at least one crop-yield enhancement product are substituted for the CLOMAZONE, as the active ingredient.

Studies and Reports

Various experimental studies and reports have been generated, regarding the performance, efficacy, and use of the micro-encapsulated extruded granules of the present invention. Below are summaries of these studies and reports.

1. Volatility Study

A column method, developed by Farm Machinery Corporation ("FMC") was used for volatility studies. This method is undertaken over soil having a moisture content of 6%–8%, which is typical for the surface of a crop field under good growing conditions. In undertaking this test, subject soil was spread in a thin layer, and the various formulations were applied to the soil surface at a rate of 2 kg a.i./ha. This rate is more than double the standard rate, and is intended to simulate a worst case condition. All formulations were applied at this same elevated rate, so accurate comparisons could be made. The liquid formulations were sprayed over the soil, whereas the extruded granules were spread or dispersed over the soil.

Air flows were established through columns, passing across the surface of the subject soil. The air flow carried any released or volatized CLOMAZONE to a collection device. After an 18 hour collection period, the amount of CLOMAZONE is assessed with a immunoassay specific for CLOMAZONE. The results of this study, using the three formulations set forth below, were as follows:

| Formulation | Micrograms Of CLOMAZONE | Percent |
|---|---|---|
| Command 4 EC (emulsified concentrate) | 134 | 100% (base line standard) |
| Command 3 ME (micro-encpasulated liquid) | 25 | 19% |
| Extruded Granules (solid, incorporating a micro-encapsulated liquid) | 1 | 1% |

A significant reduction of volatility was demonstrated by the extruded granules of the present invention as compared to the Command 4 EC and the Command 3 ME products. Early experiments that were conducted using Command 3 ME applied as a coating on various solid carriers, with and without additional filming or coating materials, did not reduce the volatility of the active ingredient expelled from solid carrier granules. In fact, several formulations significantly increased the rate of volatility. This was an unexpected result. However, by blending and mixing the Command 3 ME product uniformly throughout the solid carrier material, the volatility rate was drastically reduced to nearly zero.

Binders in the form of coating agents or film-forming polymers can also be applied to the exterior or exposed portion of the extruded granule, further to reduce volatility and attrition. These coating or film-forming agents must be selected from chemical groups which will allow the diffusion of the active ingredient from the extruded granule, once it has been applied to the target area. In the case of water-seeded rice, this diffusion must take place in water. Further, these coating agents must not be antagonistic to the efficacy of the active ingredient or create detrimental environmental effects themselves.

2. Water Solubility/Dispersibility Study

An aquatic release study was conducted using the extruded granules of the present invention, to determine whether a particular active ingredient, CLOMAZONE, would release from a water-immersed extruded granule.

A standard preparation was prepared by measuring 25 milligrams of CLOMAZONE standard into a tared 100 milliliter flask and diluted to volume with diluting solution. This flask was left standing for 24 hours without mixing.

Two hundred milligrams of the granules were placed in a hundred milliliter volumetric flask. The flask was diluted to volume with Milli-Q water. The flask was also left for 24 hours without mixing. After 24 hours, a portion of the test water was filtered through a 0.45 micron nylon filter.

A determination of CLOMAZONE in the solutions was made by injecting aliquot samples of the standard preparation and the test water into a HPLC (High Pressure Liquid Chromatography) unit. The HPLC equipment and operating conditions were:

| Column: | Prodigy ODS (3) 100A, 250 mm × 4.6 mm × 5 mm |
|---|---|
| Detection: | UV @ 230 nm |
| Flow Rate: | 1.3 ml/minute |
| Injection Volume: | 10 ml |
| Mobile Phase: | 55:30:15 (0.1% Phosphoric Acid in water: Acetonitrile:Methanol). |

Calculation:

Mg/ml CLOMAZONE=(Sample Area)(Standard Preparation, mg/ml)/(Standard Area)

Results:

Water solubility and dispersal of the extruded granules was 0.0494 mg/ml.

This is adequate for efficacy.

3. Attrition Study

A laboratory study was conducted to compare the attrition of the extruded granules of the present invention to granules which were coated with CLOMAZONE and various film forming materials such as cross-linked polysaccharides, lignosulfonates, acrylic polymers, emulsified waxes and oils. The granules of the present invention exhibited a significant reduction in attrition, as compared to the coated granules. More specifically, the granules of the present invention maintained a 99.5% solid form, with only 0.5% dust particles formed during the test.

4. Field Studies

Various rice crop agricultural sites in California were selected for experimental testing of the extruded granules. These sites also contained watergrass varieties which were resistant and non-resistant to conventional herbicides. An application rate of 12 pounds of the granules per acre of land was used, and the timing range of the application varied from planting to the two leaf stage of the developing rice seedling.

Field Study A

Granules made in accordance with Example 1 were applied to one leaf rice seedlings in a rice field in Colusa, Calif. Off-target drift was limited to the edge of the field not exceeding 10 feet. Off-target weeds were radish, mustard and Johnson grass. All weeds and potential susceptible plants past 10 feet showed no symptoms of product application. Efficacy as of a month after application was 100% sprangletop control and 98% control of resistant watergrass that was beneath the water level, at the time of application. For resistant watergrass above the water at the time of application, 78% of weed control was achieved. As to phytotoxicity, less than 5% bleaching occurred to the rice, and lasted only 4–5 days. The aerial applicator personnel reported that no dust at mixing or during application was noted, using the subject extruded granules. The granules were reported as flowing evenly through the swath master, and providing a uniform 70 foot swath at a 130 mph application speed.

Field Study B

Granules made in accordance with Example 1 were applied to ½ leaf rice seedlings in a rice field in Glenn County, Calif. Off-target drift was limited to 5 feet from the edge of the field. Bio indicator sensitive tomato plants were planted 3–5 feet from the edge of the field. Resistant watergrass and sprangetop control three weeks after application achieved 99%. Plant injury or phytotoxicity was limited to an area representing less than 10% of the field acreage. Of this affected acreage, the amount of bleaching to the rice plants was insignificant, and the plants grew out of the symptoms within 5 days after the symptoms were first noticed. The aerial applicator personnel reported the same findings and outcome as with Field Study A.

Field Study C

Granules made in accordance with Example 1 were applied to ½ leaf rice seedlings in a rice field in Glenn County, Calif. Off-target susceptible crop was a prune orchard that paralleled the north side of the rice field. Twelve days after the application, no visual symptoms of damage has been noted, either on the prune tree leaves or the fruit. Resistant watergrass control twelve days after application achieved a 95% rate, and sprangetop control by the same date achieved 100%. Less than 5% bleaching to the rice plants was noted. Symptoms were short term, and only last 5 days after first being noted.

It will be appreciated that we have disclosed a delivery system for pesticides and crop-yield enhancement products using granules extruded from a composition including at least one active ingredient, which may be micro-encapsulated, a solid carrier, and a binder, in which the granules demonstrate: reduced volatility, reduced primary drift, and reduced dust when loading, mixing, and applying; excellent control of watergrass and sprangletop; insignificant plant injury, with no long term deleterious effects; ease in loading, mixing and applying; and, flexibility in allowing various combinations of pesticides and crop-yield enhancement products in a single granular product, thereby providing multiple benefits to a crop field with a single application of product.

What is claimed is:

1. A process for making an extruded granule for delivering an agricultural chemical to a crop, comprising the steps of:
   a. blending micro-encapsulated CLOMAZONE with a solid carrier, forming a blended composition;
   b. extruding said blended composition through a die, forming extruded granules;
   c. coating said extruded granules with a solution containing a binder; and,
   d. dehydrating the coated granules to a relative moisture content of 1%–0%.

2. A process as in claim 1 further including the step of blending at least one additional micro-encapsulated active ingredient with said blended composition, said additional active ingredient selected from the group including an herbicide, an insecticide, a fungicide, a plant growth regulator, an insect growth regulator, a micronutrient, a fertilizer.

3. A process for making an extruded granule for delivering an agricultural chemical to a crop, comprising the steps of:
   a. blending micro-encapsulated CLOMAZONE with a solid carrier, forming a blended composition;
   b. extruding said blended composition through a die, forming extruded granules;
   c. coating said extruded granules with a solution containing a binder and a dispersant; and,
   d. dehydrating the coated granules to a relative moisture content of 1%–10%.

4. A process claim 3 further including the step of blending at least one additional micro-encapsulated active ingredient with said blended composition, said additional active ingredient selected from the group including an herbicide, an insecticide, a fungicide, a plant growth regulator, an insect growth regulator, a micronutrient, a fertilizer.

5. A process for making an extruded granule for delivering an agricultural chemical to a crop, comprising the steps of:
   a. blending micro-encapsulated CLOMAZONE with a solid carrier and a binder, forming a blended composition;
   b. extruding said blended composition through a die, forming extruded granules; and,
   c. dehydrating said extruded granules to a relative moisture content of 1%–10%.

6. A process as in claim 5, further including the step of blending at least one additional micro-encapsulated active ingredient with said blended composition, said additional active ingredient selected from the group including an herbicide, an insecticide, a fungicide, a plant growth regulator, an insect growth regulator, a micronutrient, a fertilizer.

7. A process for making an extruded granule for delivering an agricultural chemical to a crop, comprising the steps of:
   a. blending micro-encapsulated CLOMAZONE with a solid carrier, a binder, and a dispersant, forming a blended composition;
   b. extruding said blended composition through a die, forming extruded granules; and,
   c. dehydrating said extruded granules to a relative moisture content of 1%–10%.

8. A process as in claim 7, further including the step of blending at least one additional micro-encapsulated active ingredient with said blended composition, said additional active ingredient selected from the group including an herbicide, an insecticide, a fungicide, a plant growth regulator, an insect growth regulator, a micronutrient, a fertilizer.

* * * * *

UNITED STATES PATENT AND TRADEMARK OFFICE
CERTIFICATE OF CORRECTION

PATENT NO. : 6,797,277 B2
DATED : September 28, 2004
INVENTOR(S) : John L. Heier et al.

It is certified that error appears in the above-identified patent and that said Letters Patent is hereby corrected as shown below:

<u>Column 10,</u>
Line 65, "1%-0%" should be -- 1%-10% --.

Signed and Sealed this

Ninth Day of August, 2005

JON W. DUDAS
*Director of the United States Patent and Trademark Office*